(12) United States Patent
Rothermel et al.

(10) Patent No.: US 9,272,109 B2
(45) Date of Patent: Mar. 1, 2016

(54) CUSHION COUPLING ASSEMBLY

(75) Inventors: Justin Edward Rothermel, Monroeville, PA (US); Michael Edward Hucko, Monroeville, PA (US); Chad Zediker, Greensburg, PA (US); Richard T. Haibach, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 419 days.

(21) Appl. No.: 13/131,618

(22) PCT Filed: Nov. 21, 2009

(86) PCT No.: PCT/IB2009/055250
§ 371 (c)(1),
(2), (4) Date: May 27, 2011

(87) PCT Pub. No.: WO2010/067238
PCT Pub. Date: Jun. 17, 2010

(65) Prior Publication Data
US 2011/0226255 A1    Sep. 22, 2011

Related U.S. Application Data

(60) Provisional application No. 61/122,133, filed on Dec. 12, 2008.

(51) Int. Cl.
*A61M 16/06* (2006.01)
*A62B 9/04* (2006.01)

(52) U.S. Cl.
CPC ............ *A61M 16/06* (2013.01); *A61M 16/0605* (2014.02); *A61M 16/0633* (2014.02); *A62B 9/04* (2013.01)

(58) Field of Classification Search
CPC . A61M 16/00; A61M 16/06; A61M 16/0605; A61M 16/0633; A61M 16/08; A61M 16/0816; A61M 16/0875; A61M 39/10; A61M 2039/1027; A62B 9/04
USPC ............ 128/206.21, 206.24, 206.26, 206.28, 128/201.22, 201.23, 202.27, 204.18, 205.25
See application file for complete search history.

(56) References Cited

U.S. PATENT DOCUMENTS

| | | | |
|---|---|---|---|
| 6,530,373 B1* | 3/2003 | Patron et al. | 128/205.25 |
| 6,817,362 B2* | 11/2004 | Gelinas et al. | 128/206.17 |
| 6,823,869 B2* | 11/2004 | Raje et al. | 128/206.24 |
| 2006/0249159 A1* | 11/2006 | Ho et al. | 128/207.13 |

(Continued)

FOREIGN PATENT DOCUMENTS

| | | |
|---|---|---|
| EP | 1982740 A2 | 10/2008 |
| WO | WO0211804 A2 | 2/2002 |
| WO | WO2007104042 A2 | 9/2007 |

OTHER PUBLICATIONS

Detent definition; Dictionary.com.*

*Primary Examiner* — Justine Yu
*Assistant Examiner* — Colin W Stuart
(74) *Attorney, Agent, or Firm* — Michael W. Haas

(57) ABSTRACT

Various embodiments of a respiratory interface device, such as a mask, that includes a substantially rigid frame member and a cushion device wherein the frame member and cushion device are coupled together using a clip assembly wherein the clip assembly includes a plurality of tabs and a plurality of detents. The detents and tabs engage with one another to removably couple the cushion device to the frame member.

16 Claims, 6 Drawing Sheets

(56) References Cited

U.S. PATENT DOCUMENTS

| | | |
|---|---|---|
| 2008/0053450 A1 | 3/2008 | Van Kerkwyk et al. |
| 2008/0072909 A1 | 3/2008 | Sherman |
| 2008/0302361 A1* | 12/2008 | Snow et al. .............. 128/202.27 |
| 2010/0108072 A1* | 5/2010 | D'Souza et al. ......... 128/206.24 |

* cited by examiner

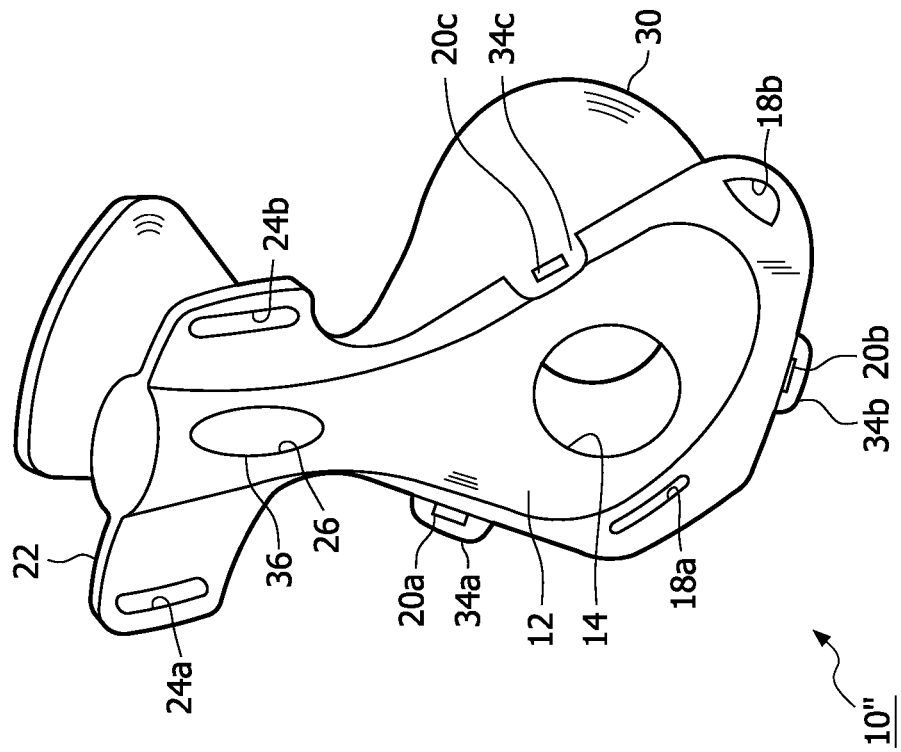
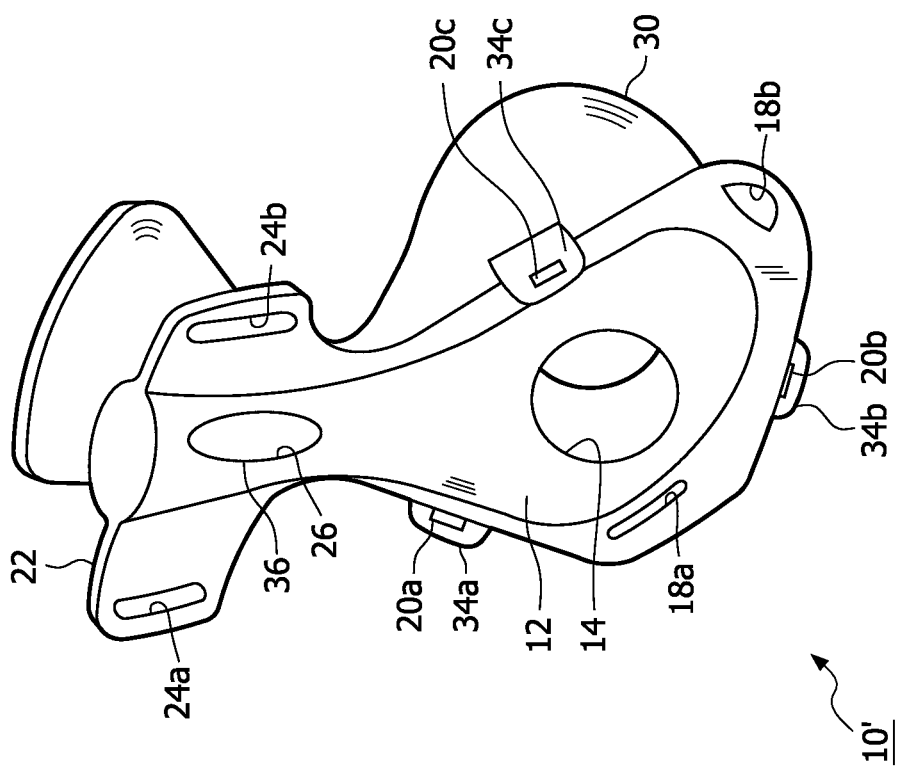

CUSHION COUPLING ASSEMBLY

CROSS-REFERENCE TO RELATED APPLICATIONS

This patent application claims the priority benefit under 35 U.S.C. §119(e) of U.S. Provisional Application No. 61/122,133 filed on Dec. 12, 2008, the contents of which are herein incorporated by reference.

BACKGROUND OF THE INVENTION

1. Field of the Invention

The present invention relates to respiratory interface devices, and, in particular, to a respiratory interface device, such as a mask, that includes a frame member and a cushion device, wherein the frame member and cushion device are coupled together using a clip assembly employing a plurality of tabs and corresponding detents.

2. Description of the Related Art

A variety of respiratory masks are known that cover the areas surrounding the nose and/or mouth of a human user and that are designed to create an effective fit against the user's face. Typically, air, gas, or a combination thereof can be provided at a positive pressure within the mask for consumption by the user. The uses for such masks include high altitude breathing (aviation applications), swimming, mining, fire fighting and various medical diagnostic and therapeutic applications.

One requisite of many of these masks, particularly medical respiratory masks, is that they provide a fit against the user's face that is effective to provide therapy or delivery of air and/or gas as mentioned herein and that the mask contours with the user's face to limit or prevent leakage of the air and/or gas being supplied. A known mask typically includes a faceplate constructed of a substantially rigid material selected from a variety of such materials known in the art, including, without limitation, polycarbonate, nylon and acrylonitrile butadiene styrene (ABS), and a cushion portion constructed of a substantially flexible material selected from a variety of such materials known in the art, including, without limitation, silicone.

The cushion portion is attached to the faceplate and the cushion portion functions to space the faceplate away from the user's face such that the soft cushion portion, and not the rigid faceplate, contacts the user's face to provide an effective fit. The space provided between the faceplate and the user's face forms a chamber for receiving gas from an external gas source for consumption by the user. It is important that the faceplate and cushion portion are connected using a mechanism that provides a tight seal such as to prevent leakage of the air and/or gas being supplied to the user.

Various mechanisms are known in the art to attach the faceplate and cushion portion. In one example, glue may be used to hold together the faceplate and cushion portion. The use of glue results in a mask wherein the cushion portion cannot be easily removed from the faceplate for cleaning. In another example, a tongue and groove assembly is used to connect a mask faceplate to a mask cushion portion. The faceplate can have a rim that includes an outwardly extending flange that engages with a corresponding rim on the cushion portion. The faceplate rim can further include a tongue which protrudes rearwardly from the back of the faceplate and is received in a corresponding complementary shaped groove or recess formed in rim of the cushion portion. A disadvantage of this type of tongue and groove assembly is that it can be complex to manufacture.

SUMMARY OF THE INVENTION

Accordingly, it is an object of the present invention to provide a respiratory interface device that overcomes the shortcomings of conventional respiratory interface device. This object is achieved according to one embodiment of the present invention by providing a respiratory interface device that a faceplate having a plurality of tabs spaced apart on a peripheral edge of the faceplate and projecting outwardly therefrom and a cushion device including a plurality of detents. Each of the plurality of detents have at least one opening formed therein. The plurality of detents are spaced apart on a peripheral edge of the cushion device and project forwardly relative to the peripheral edge of the cushion device. Each of the plurality of detents engages a corresponding one of the tabs to removably couple the cushion device to the faceplate.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 6A and 6B are side isometric views of a respiratory mask according to alternative embodiments of the invention.

DESCRIPTION OF THE EXEMPLARY EMBODIMENTS

Figure 1:
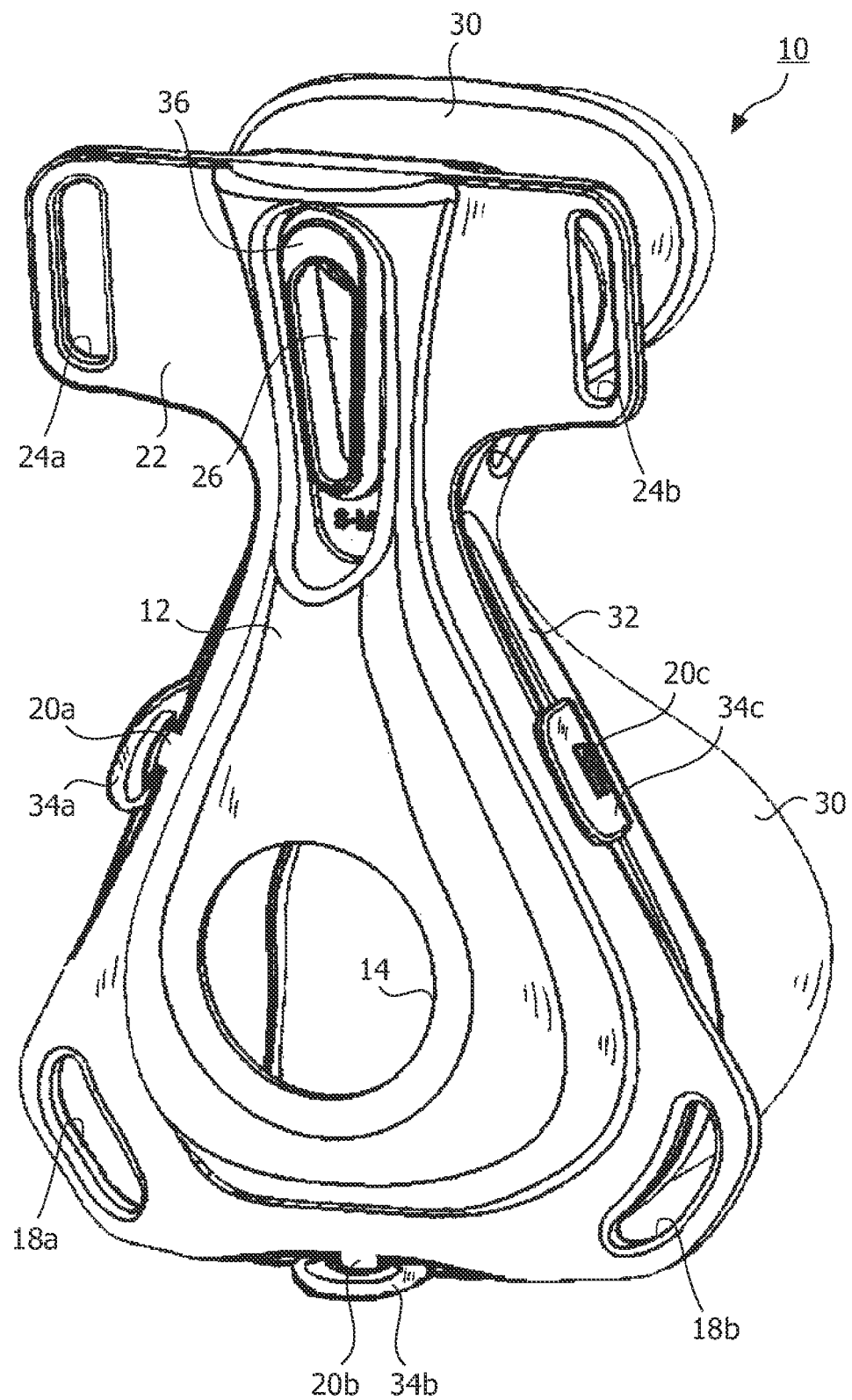
FIG. 1 is a front isometric view of a respiratory mask according to an embodiment of the invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the term "respiratory interface device" refers to any suitable mechanism for transporting gas to and/or from the airway of a user, such as a patient, the gas may be pressurized (e.g., positive airway pressure) or may not be pressurized, and expressly includes, but is not limited to, non-invasive respiratory interfaces such as masks (e.g., without limitation, masks including support elements such as forehead supports and cheek pads and full face masks such as the Total™ face mask sold by the assignee hereof).

As employed herein, the statement that two or more parts or components are "coupled" or "connected" together shall mean that the parts are joined or operate together either directly or through one or more intermediate parts or components. Also, as employed herein, the term "number" shall mean one or an integer greater than one (i.e., a plurality).

FIG. 1 is an isometric view of a respiratory mask 10 according to a particular, non-limiting embodiment of the invention. Respiratory mask 10 includes a frame member in the form of a faceplate 12. The particular faceplate 12 shown in FIG. 1 is not meant to be limiting and it should be understood that other types of frame members (e.g., rigid and semi-rigid) that hold together various components of a mask assembly may be substituted for the faceplate 12.

Figure 2:
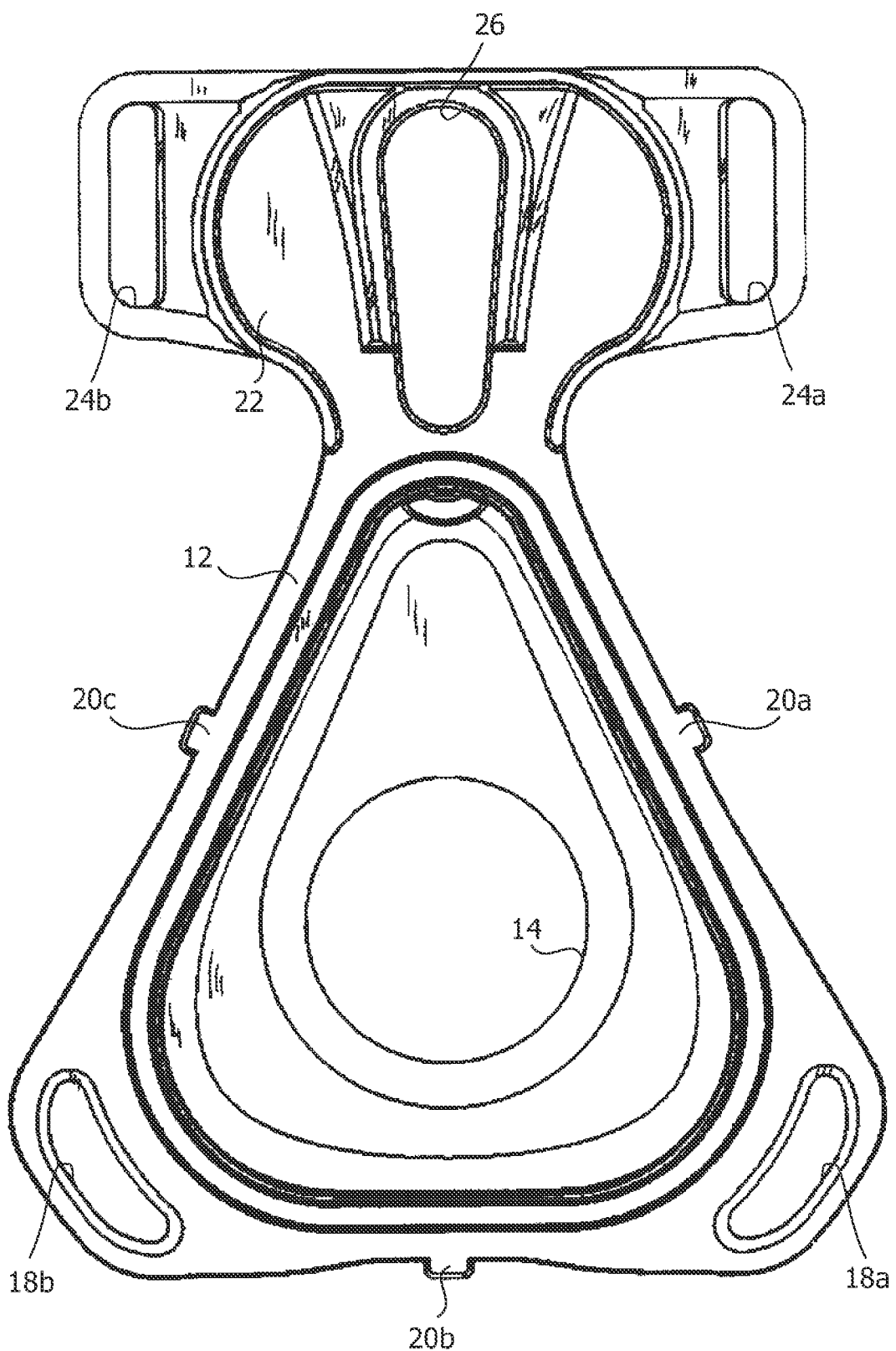
FIG. 2 is a rear elevational view of a faceplate of the respiratory mask shown in FIG. 1.

FIG. 2 is a rear elevational view of faceplate 12. Faceplate 12 in the illustrated embodiment is generally triangular in shape and is typically, although not necessarily, made of a substantially rigid material. Suitable rigid materials for use in constructing faceplate 12 include such materials known in the art, for example, without limitation, polycarbonate, nylon, ABS and combinations thereof.

As shown in FIGS. 1 and 2, faceplate 12 also defines an opening 14. Opening 14 can function as an air inlet. The air inlet can be coupled to a coupling device, such as a swivel conduit (not shown), for carrying air and/or gas between the mask 10 and an external air and/or gas source (not shown), such as a blower or other suitable device. It is to be understood that the present invention contemplates a variety of different coupling devices that could be attached, either permanently or selectively, to opening 14 to carry air and/or gas to or from mask 10.

Also, as shown in FIGS. 1 and 2, faceplate 12 defines two slits 18a, 18b located on opposite, lower corners (of the triangle) of faceplate 12. Each of slits 18a, 18b is structured to receive a strap (not shown) therethrough. It is contemplated that the straps can be attached to a headgear (not shown) or can be fitted around the user's head to secure mask 10 to the face of the user. Although, slits are used to couple the headgear to the faceplate, the present invention contemplates using any suitable headgear coupling assembly to accomplish this function.

Faceplate 12 includes tabs 20a, 20b, 20c positioned on the outer peripheral edge of the faceplate 12 and extending outwardly therefrom. In the particular embodiment of FIGS. 1 and 2, each of tabs 20a, 20b, 20c is located on a respective one of the sides (of the triangle) of the faceplate 12. The purpose of tabs 20a, 20b, 20c is described in detail elsewhere herein.

Also, as shown in FIGS. 1 and 2, faceplate 12 includes a forehead support 22 connected to and extending upwardly from the main body of the faceplate. In the illustrated exemplary embodiment, forehead support 22 includes two slits or openings 24a, 24b positioned on opposite sides of the forehead support. Slits 24a, 24b are each structured to receive a strap (not shown) extending therethrough to assist in holding the mask 10 in place on the user's face. As with slits 18a, 18b, other techniques for coupling a headgear to the forehead support are contemplated by the present invention. Forehead support 22 further includes a slit or opening 26. The function of opening 26 is described in more detail elsewhere herein.

It is contemplated that forehead support 22 is an optional feature of mask 10. Thus, alternatively, mask 10 could include a faceplate that does not include forehead support 22 (i.e., include only the generally triangular main body portion of the faceplate 12). Forehead support 22 is shown for illustrative purposes as one particular type of facial support. It should be understood that other particular types of forehead supports and other types of facial supports, such as, without limitation, cheek pads, can be used in place of or in addition to the forehead support.

Referring to FIG. 1, mask 10 further includes a soft, flexible cushion portion 30 that is coupled to the back of faceplate 12 and extends rearwardly therefrom. Suitable soft, flexible materials for use in constructing cushion portion 30 include, but are not limited to, silicone and other like materials. Cushion portion 30 is structured to extend toward the user's face and generally defines the depth of mask 10. The shape of cushion portion 30 typically, but not necessarily, corresponds to the shape of faceplate 12. Thus, in the illustrated embodiment, cushion portion 30 is generally triangular in shape to correspond to faceplate 12 shown in FIGS. 1 and 2 that is generally triangular in shape. In addition, in the illustrated embodiment, cushion portion 30 includes a portion that corresponds to the forehead support 22.

Also, as shown in FIG. 1, a substantially rigid ring 32 is coupled to (such as by an overmolding process or by using a suitable adhesive) and extends around the outer peripheral edge of the portion of cushion portion 30 that corresponds to the triangular main body of faceplate 12. Thus, in the embodiment, ring 32 has a generally triangular shape. Suitable materials for use in constructing ring 32 can include those materials previously described for use in constructing faceplate 12. As shown in FIG. 1, detents 34a, 34b, 34c are positioned on the outer peripheral edge of ring 32, and protrude forwardly therefrom.

Detents 34a, 34b, 34c are each spaced apart and positioned on a respective side of (triangular) ring 32 to correspond with tabs 20a, 20b, 20c, respectively, of faceplate 12. In alternate embodiments, detents 34 may be positioned at various locations on the outer peripheral edge of ring 32 and tabs 20 may be positioned at various locations on the peripheral edge of faceplate 12. For example, one or more detents 34 may be positioned on the outer peripheral edge of at least two of any sides of ring 32, and one or more tabs 20 may be positioned correspondingly on the peripheral edge of at least two of any sides of the faceplate 12. As shown in FIG. 1, each of detents 34a, 34b, 34c has an opening formed therein for engaging one of the tabs 20a, 20b, 20c, respectively, as described in greater detail elsewhere herein. In an alternate embodiment, each of detents 34 may have more than one opening formed therein for engaging more than one tab 20.

Also, as shown in FIG. 1, opening 26 in forehead support 22 is structured to engage a portion of cushion portion 30 to assist in coupling the cushion portion to the forehead support. In particular, a portion 36 of cushion portion 30 is passed through from the back side to the front side of opening 26 and folded over a peripheral edge of the front side of the opening. The peripheral edge of the front side of opening 26 protrudes outward relative to the surface of forehead support 22 such that portion 36 of cushion portion 30 is folded over the protruding peripheral edge to at least partially couple the cushion portion to faceplate 12.

Alternatively, or in addition to opening 26, it is contemplated that additional tabs 20 could extend outwardly from the outer peripheral edge of forehead support 22 (the additional tabs could be spaced apart and positioned on the sides and/or top of the forehead support 22). Further, it is contemplated that ring 32, rather than being triangular in shape to correspond to the main body of faceplate 12, could instead also extend along the outer peripheral edge of the portion of the cushion portion 30 which extends in back of forehead support 22, and could include additional spaced detents 34 extending forwardly therefrom for engaging respective ones of additional tabs 20 just described.

Figure 3:
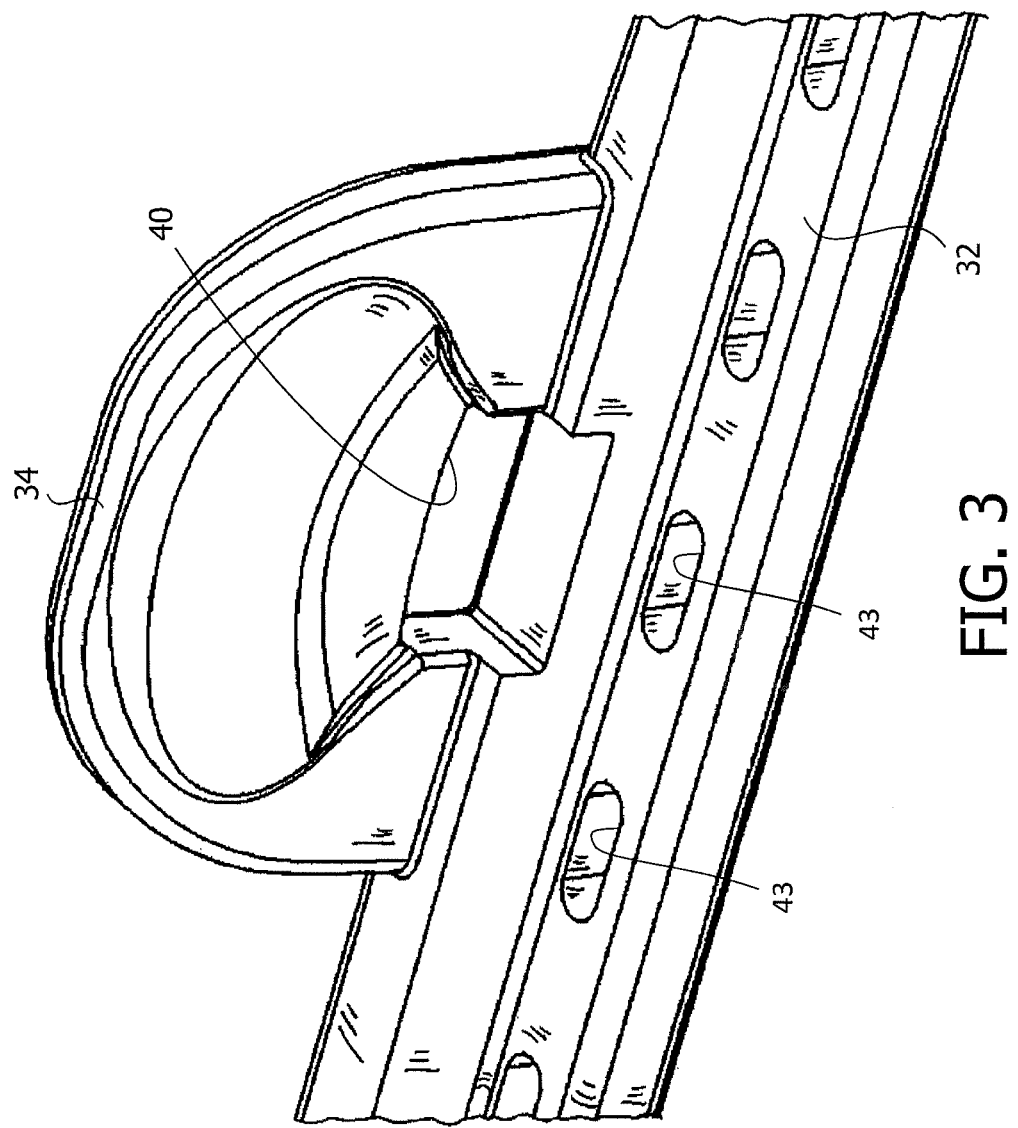
FIG. 3 is an enlarged isometric view of a detent of the cushion portion of the respiratory mask shown in FIG. 1.
Figure 4A:
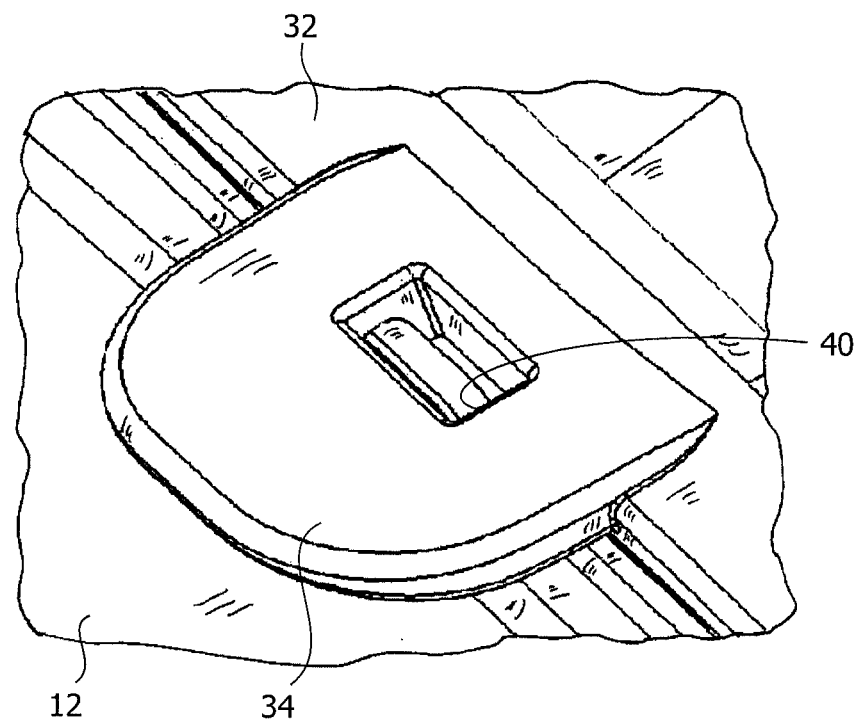
FIGS. 4A and 4B are enlarged isometric views of a detent-tab assembly of the respiratory mask shown in FIG. 1.
Figure 4B:
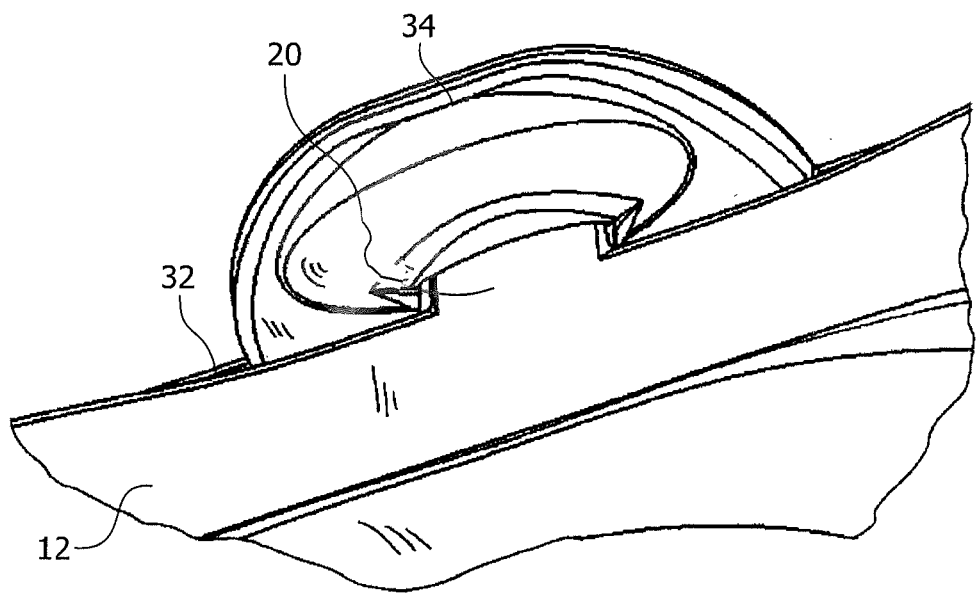

The apparatus of the coupling assembly including cooperating tabs 20 and detents 34 will now be described in connection with FIGS. 3, 4A, and 4B. FIG. 3 is an enlarged isometric view of a portion of cushion portion 30, and specifically ring 32 and a detent 34 extending forwardly therefrom. Preferably, each of detents 34 is formed as an integral part of ring 32. As shown in FIG. 3, each detent 34 includes an opening 40. Opening 40 is sized to receive a corresponding one of tabs 20 as shown in FIGS. 4A and 4B. As previously described herein, in one embodiment, each detent 34 may have more than one opening 40 sized to receive more than one corresponding tab 20.

In particular, FIG. 4A is a view from the outside of detent 34 and FIG. 4B is a view from the inside of the detent showing tab 20 received therein. According to an aspect of the present invention, it is contemplated that cushion portion 30 will be securely coupled to faceplate 12 as a result of a tension force applied by the flexible cushion portion when each of tabs 20 is received within the corresponding one of the detents 34. In particular, cushion portion 30 will be stretched and flexed outwardly and upwardly when each of the detents 34a, 34b, 34c is pulled and placed over the corresponding tab 20a,b,c. When the pulling force is released, each detent 34a, 34b, 34c will engage the received tab 20a, 20b, 20c and will be held in place by the resulting elastic force of cushion portion 30.

In another embodiment, cushion portion 30 may be molded to a flexible ring 32. The cushion portion and flexible ring 32 can be stretched and flexed outwardly and upwardly when each of the detents 34 is pulled and placed over the corresponding tab 20a, 20b, 20c. When the pulling force is released (and the cushion portion 30 and flexible ring 32 resume their shape prior to being stretched and flexed), each detent 34a,b,c will engage the received tab 20a, 20b, 20c and will be held in place by the resulting elastic force of the cushion portion 30 and flexible ring 32.

According to one particular embodiment, cushion portion 30 is attached to the ring 32 by employing an overmolding process. In particular, referring to FIG. 3, ring 32 in this embodiment further includes a plurality of opening or slits 43 that are spaced apart and extend around the perimeter of the ring. During the overmolding process, the material forming cushion portion 30 (e.g., a silicon material) passes through or into the plurality of slits and is formed therein so as to physically attach or bond the cushion portion to the ring.

It is contemplated that detents 34 (e.g., 34a, 34b, 34c as shown in FIGS. 1, 3, 4A and 4B) can be of various shapes and sizes, and the number employed can vary. For example, a detent 34 may have a scalloped or seashell shape as described in further detail elsewhere herein. Further, detents 34 may be placed at varying angles relative to ring 32. In addition, opening 40 provided in each detent 34 also can be of various shapes and sizes, and more than one opening 40 can be provided within a detent 34. For example a detent 34 can include two openings 40 structured to engage two corresponding tabs 20. Furthermore, tabs 20 (e.g., 20a, 20b, 20c as shown in FIGS. 1, 2, 4A, and 4B) can be of various shapes, sizes and number. For example, a tab 20 may have a scalloped or seashell shape.

Figure 5:
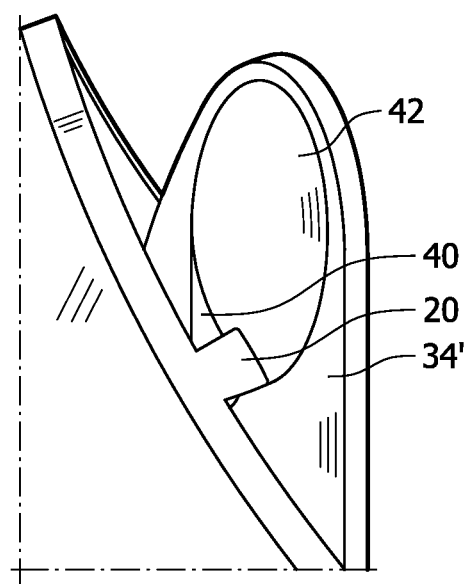
FIG. 5 is a side isometric view of a detent-tab assembly according to an alternative embodiment of the invention.

In particular, FIG. 5 is a side isometric view of a detent-tab assembly employing an alternative detent 34', from the inside of the detent 34'. Detent 34' has a scalloped recess 42 formed therein. It is contemplated that scalloped recess 42 will facilitate the engagement of tab 20 into opening 40 of detent 34'. For example, tab 20 may be pressed against the upper inside surface of detent 34' and recess 42 formed in detent 34' will guide the tab downward and into opening 40.

FIGS. 6A and 6B are side isometric views of respiratory masks 10' and 10", respectively, according to alternative embodiments of the invention. Masks 10' and 10" are similar to mask 10 shown in FIG. 1, and therefore, as seen in FIGS. 6A and 6B, include a number of the same parts including cushion portion 30, faceplate 12, opening 14, slits 18a,18b, tabs 20a, 20b, 20c, forehead support 22, slits 24a, 24b, opening 26, detents 34a, 34b, 34c, and portion 36. Masks 10' and 10" do not, however, include a ring 32 coupled to the cushion portion 30 as shown in FIG. 2. Instead, as shown in FIG. 6A, mask 10' includes a cushion portion 30 having detents 34a, 34b, 34c directly coupled to the cushion portion 30 instead of the detents 34a, 34b, 34c being coupled to the ring 32. Detents 34a, 34b, 34c can be coupled to the cushion portion 30 using a wide variety of conventional techniques known in the art such as various molding processes. Detents 34a,b,c can be made of a substantially rigid or semi-rigid material.

As a further alternative, as shown in FIG. 6B, the mask 10" includes a cushion portion 30 having detents 34a,b,c integrally formed with cushion portion 30. Detents 34a,b,c are formed as part of the cushion portion 30 when cushion portion 30 is molded and thus the detents will be made of the same substantially flexible material as the cushion portion. As was the case with mask 10, in masks 10' and 10", whatever the design of detents 34 happens to be, cushion portion 30 will be securely coupled to faceplate 12 as a result of a tension force after each tab 20 is received within the corresponding detent 34.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory interface device comprising:
   a frame member having a plurality of tabs spaced apart on a peripheral edge of the frame member and projecting outwardly therefrom; and
   a cushion device including a plurality of detents, each of the plurality of detents being spaced apart on a peripheral edge of the cushion device and projecting forwardly from the peripheral edge of the cushion device, each of the plurality of detents having an inside surface perpendicular to the peripheral edge of the cushion device, an outside surface perpendicular to the peripheral edge of the cushion device and an opening formed therethrough, wherein each of the detents has a curved recessed surface formed therein and located between the inside surface and the outside surface to thereby provide a guide to position each of the plurality of tabs downward into the opening of a corresponding one of the plurality of detents, and wherein each of the plurality of detents is positioned to engage with a corresponding one of the plurality of tabs to removably couple the cushion device to the frame member.

2. The respiratory interface device of claim 1, wherein the cushion device comprises a cushion portion and a ring coupled to the cushion portion, wherein the ring comprises the peripheral edge of the cushion device, and wherein the detents project forwardly relative to the ring.

3. The respiratory interface device of claim 2, wherein the ring and the detents are integrally formed and are constructed of a substantially rigid material.

4. The respiratory interface device of claim 2, wherein the cushion portion and the ring are coupled together by over-molding the cushion portion to the ring.

5. The respiratory interface device of claim 2, wherein the ring has three sides, and wherein the plurality of detents includes three detents, each of the detents being positioned on a different side of the ring.

6. The respiratory interface device of claim 1, wherein the cushion device comprises a cushion portion, and wherein the detents are directly attached to the cushion portion.

7. The respiratory interface device of claim 6, wherein the plurality of detents includes three detents.

8. The respiratory interface device of claim 7, wherein each of the three detents is positioned on a different side of the cushion device.

9. The respiratory interface device of claim 1, wherein the cushion device comprises a cushion portion, and wherein the detents are integrally formed as part of the cushion portion.

10. The respiratory interface device of claim 1, wherein said frame member includes a forehead support member.

11. The respiratory interface device of claim 10, wherein the forehead support member includes an opening defined by a peripheral edge, and wherein a portion of the cushion device is received through the opening of the forehead support member and engages the peripheral edge of the opening of the forehead support member.

12. The respiratory interface device of claim 1, wherein the cushion device comprises a cushion portion constructed of a substantially flexible material.

13. The respiratory interface device of claim 12, wherein the substantially flexible material is a silicon material.

14. The respiratory interface device of claim 1, wherein the frame member includes three sides, and wherein the plurality of tabs includes three tabs, each tab being positioned on a different side of the frame member.

15. The respiratory interface device of claim 1, wherein the frame member has a first opening comprising an inlet.

16. The respiratory interface device of claim 1, wherein the inside surface and the outside surface of each detent defines a thickness of each detent that is less than a thickness of the peripheral edge of the cushion device.

* * * * *